US012788724B2

(12) United States Patent
Okuda et al.

(10) Patent No.: US 12,788,724 B2
(45) Date of Patent: Nov. 10, 2026

(54) COATED API PARTICLES

(71) Applicant: TOWA PHARMACEUTICAL CO., LTD., Osaka (JP)

(72) Inventors: Yutaka Okuda, Kadoma (JP); Isamu Saeki, Kadoma (JP); Tatsuya Honjo, Kadoma (JP); Kayo Yuminoki, Kadoma (JP)

(73) Assignee: TOWA PHARMACEUTICAL CO., LTD., Osaka (JP)

( * ) Notice: Subject to any disclaimer, the term of this patent is extended or adjusted under 35 U.S.C. 154(b) by 690 days.

(21) Appl. No.: 17/802,510

(22) PCT Filed: Feb. 25, 2021

(86) PCT No.: PCT/JP2021/006977

§ 371 (c)(1),
(2) Date: Aug. 25, 2022

(87) PCT Pub. No.: WO2021/172395

PCT Pub. Date: Sep. 2, 2021

(65) Prior Publication Data

US 2023/0094101 A1 Mar. 30, 2023

(30) Foreign Application Priority Data

Feb. 26, 2020 (JP) ................................ 2020-030016

(51) Int. Cl.

| | |
|---|---|
| ***A61K 9/50*** | (2006.01) |
| ***A61K 9/20*** | (2006.01) |
| ***A61K 31/4422*** | (2006.01) |

(52) U.S. Cl.

CPC ............ *A61K 9/501* (2013.01); *A61K 9/2018* (2013.01); *A61K 9/2054* (2013.01); *A61K 9/5089* (2013.01); *A61K 31/4422* (2013.01)

(58) Field of Classification Search

CPC ............. A61K 9/16; A61K 9/50; A61K 47/10
See application file for complete search history.

(56) References Cited

U.S. PATENT DOCUMENTS

| | | | |
|---|---|---|---|
| 2002/0110689 | A1 | 8/2002 | Hu et al. |
| 2017/0333359 | A1 | 11/2017 | Goldstein |
| 2019/0216742 | A1 | 7/2019 | Neikirk et al. |
| 2019/0376181 | A1 | 12/2019 | Neikirk et al. |

FOREIGN PATENT DOCUMENTS

| | | | | |
|---|---|---|---|---|
| JP | 2000191516 | A | * | 7/2000 |
| JP | 2004-043316 | A | | 2/2004 |
| JP | 2010-006780 | A | | 1/2010 |
| JP | 2010006780 | | * | 1/2010 |
| WO | 2012/116814 | A1 | | 9/2012 |
| WO | WO2013046133 | | * | 4/2013 |

OTHER PUBLICATIONS

International Search Report issued in corresponding International Patent Application No. PCT/JP2021/006977 dated Apr. 20, 2021.
Kaariainen et al., "Surface modification of acetaminophen particles by atomic layer deposition," International Journal of Pharmaceutics, 525 (1): 160-174 (2017).
Nanexa AB, "Apparatus for forming fully coated particles with a solid core," Research Disclosure, The Industry Standard Disclosure Publication Service, 669 (38): 56 (2020).

* cited by examiner

*Primary Examiner* — Robert A Wax
*Assistant Examiner* — Kimberly Barber
(74) *Attorney, Agent, or Firm* — Morgan, Lewis & Bockius LLP

(57) ABSTRACT

The present invention chiefly aims to provide a new API particle in which a metal or the like is coated on the API itself of a pharmaceutical solid dosage form.
The present invention includes, for example, a coated API particle, wherein the surface of an API particle is coated with a metal or a metal oxide (e.g., iron oxide) by sputter deposition, and a process for manufacturing a pharmaceutical solid dosage form (e.g., tablet) using the coated API particles.
According to the present invention, for example, it is possible to improve the photostability of an API itself or of pharmaceutical solid dosage forms produced with the API.

9 Claims, 2 Drawing Sheets

[Figure 1]
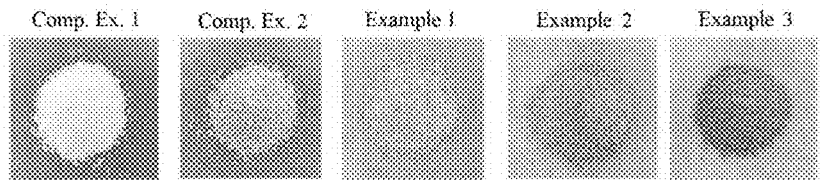
[Figure 2]
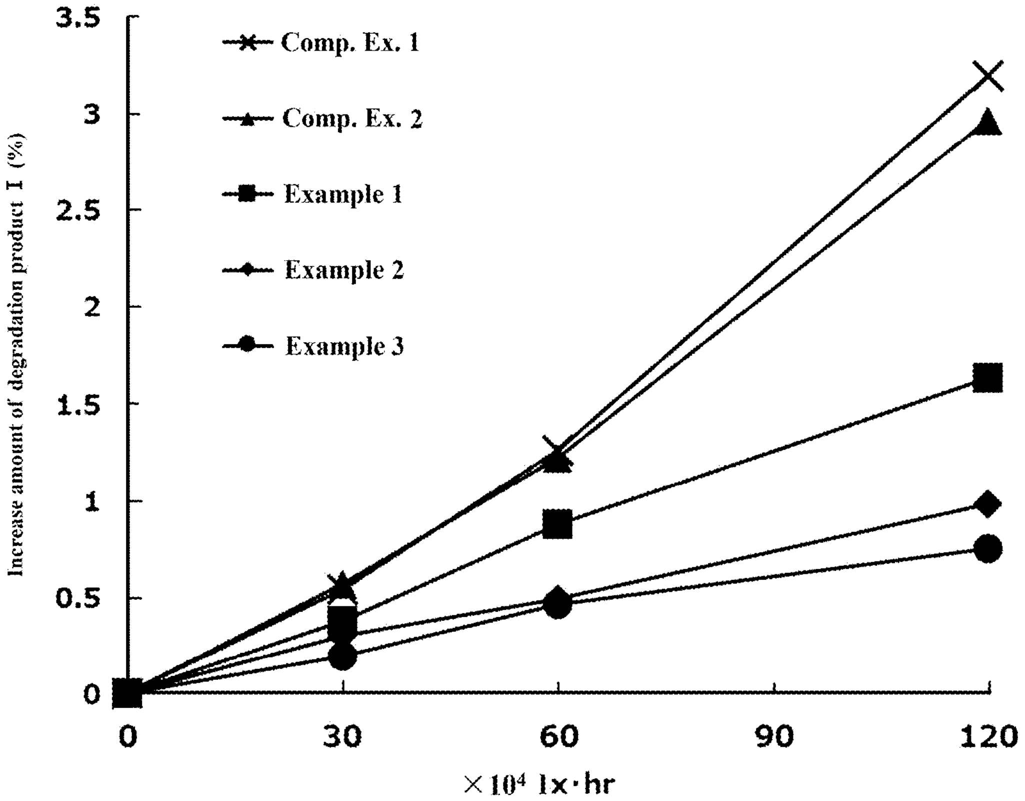

[Figure 3]
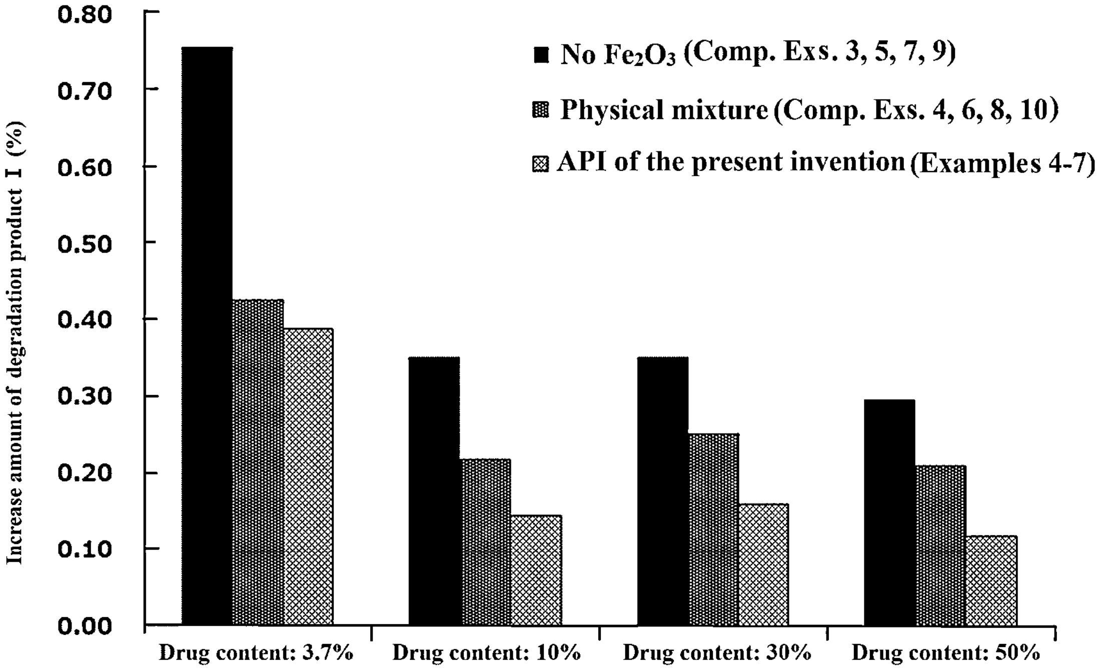

COATED API PARTICLES

CROSS-REFERENCE TO RELATED APPLICATIONS

This application claims the benefit of Japanese Patent Application No. 2020-30016, filed with the Japan Patent Office on Feb. 26, 2020. The Japanese application is hereby incorporated by reference for all purposes as if the entire application documents (specification, claims, drawings, and abstract) were expressly set forth herein.

TECHNICAL FIELD

The present invention belongs to the technical field of active pharmaceutical ingredients (API). The present invention relates to an API particle, and in particular to a coated API particle.

BACKGROUND OF THE INVENTION

Pharmaceutical solid dosage forms are usually made by preparing raw materials such as active pharmaceutical ingredients and excipients, and in the case of tablets, tablets are generally produced by tableting and molding to produce uncoated tablets. The manufactured tablets may be coated, for example, to protect the drug from atmospheric moisture, oxygen, carbon dioxide, and light; to control the release of the drug or regulate its onset of action; to mask taste and odor for ease of administration; to increase product value; or to improve identification.

The above coating has conventionally been performed in pharmaceuticals mainly by film coating or sugar coating. In film coating, an aqueous or organic solvent solution containing a polymer of a coating base (coating agent) is sprayed continuously or discontinuously onto the surface of a solid dosage form, and the moisture in the droplets that adhere to and spread on the tablet surface evaporates, causing the coating agent particles to aggregate and form a film. The coating of tablets is thus applied to the manufactured uncoated tablets.

In addition to the above, a method called atomic layer deposition (ALD) is also known as a technique for coating pharmaceutical solid dosage forms (Patent Document 1). In the atomic layer deposition method, the functional groups on the surface of the pharmaceutical dosage form react with the coating material, and a monolayer of film is deposited on the surface of the pharmaceutical dosage form. Patent Document 1 uses this atomic layer deposition method to form a layer of metal oxide with a nano-order thickness of about 0.1 to about 100 nm to coat a pharmaceutical solid dosage form containing an active ingredient.

Sputter deposition, on the other hand, is a metal deposition technology also known as dry plating or vacuum plating. An inert gas (e.g., argon) is introduced in a vacuum and a negative voltage is applied to a target (plate-shaped deposition material) to generate a glow discharge, which ionizes the atoms of the inert gas, causing the gas ions to collide with the target surface at high speed and strike the target violently. The particles (atoms and molecules) of the deposition material constituting the target are violently ejected and vigorously adhered to and deposited on the surface of the base material/substrate to form a thin film. It is applied to anti-reflection and surface protection of displays for TVs, smartphones and the like; transparent electrodes for solar cells and liquid crystal devices; provision of wear resistance; and suppression of water vapor and oxygen permeation.

Compared to the aforementioned atomic layer deposition (ALD) method, sputter deposition is characterized by stronger film adhesion and greater film stress. Furthermore, sputtering technology has the advantage that the deposited material is less prone to alteration and heat is less likely to be applied to the object.

Sputtering technology has also been applied in the field of medicine or food products in some cases. For example, Patent Document 2 discloses the formation of a metallic film made of edible metals such as gold, silver, and platinum on the surface of a granular shape, tablet shape, etc., to provide medicines and other products with excellent decorative properties. However, the invention of Patent Document 2 is not implemented from the viewpoint of shading pharmaceutical solid dosage forms from light and providing them with functionality.

PRIOR ART

Patent Document

Patent Document 1: JP, 2014-510066, A

Patent Document 2: JP, 2004-43316, A

SUMMARY OF THE INVENTION

Problem to be Solved by the Invention

For example, tablet coating, which is applied to ensure photostability and other properties, is generally applied to uncoated tablets produced by compression molding. No such coating is found on the drug substance API.

The present invention chiefly aims to provide a new API particle in which a metal or the like is coated on the API itself of a pharmaceutical solid dosage form.

Means for Solving the Problem

As a result of intensive studies, the present inventors found that the light-shielding agent can be coated on the drug substance API by using sputtering technology, and completed the present invention.

The present invention includes, for example, the following.

[1] A coated API particle, comprising a coating consisting of a metal or a metal oxide on the surface of the API particle.

[2] The coated API particle according to the [1] above, wherein the coating content of the metal or the metal oxide is in the range of 0.05% to 10% by mass.

[3] The coated API particle according to the [1] or [2] above, which has an average diameter $D_{50}$ in the range of 1 μm to 1000 μm.

[4] The coated API particle according to any one of the [1] to [3] above, wherein the metal oxide is iron oxide.

[5] The coated API particle according to any one of the [1] to [4] above, wherein the coating is performed by sputter deposition.

[6] A process for producing a coated API particle, comprising a step of coating the surface of an API particle with a metal or a metal oxide, thereby producing the coated API particle.

[7] The process according to the [6] above, wherein the average diameter $D_{50}$ of the coated API particle is in the range of 1 μm to 1000 μm.

[8] The process according to the [6] or [7] above, wherein the metal oxide is iron oxide.

[9] The process according to any one of the [6] to [8] above, wherein the coating is performed by sputter deposition.

[10] A process for manufacturing a pharmaceutical solid dosage form, comprising:

a step of coating the surface of an API particle with a metal or a metal oxide to obtain a coated API particle; and a step of formulating the dosage form using the coated API particle obtained in the preceding step to manufacture the pharmaceutical solid dosage form.

[11] The process according to the [10] above, wherein the average diameter $D_{50}$ of the coated API particle is in the range of 1 μm to 1000 μm.

[12] The process according to the [10] or [11] above, wherein the metal oxide is iron oxide.

[13] The process according to any one of the [10] to [12] above, wherein the pharmaceutical solid dosage form is a tablet.

[14] The process according to any one of the [10] to [13] above, wherein the coating is performed by sputter deposition.

[15] A pharmaceutical solid dosage form, comprising the coated API particle according to any one of the [1] to [5] above.

[16] The pharmaceutical solid dosage form according to the [15] above, wherein the pharmaceutical solid dosage form is a tablet.

[17] A method of photostabilizing an API or a pharmaceutical solid dosage form thereof, comprising a step of coating an API particle with a metal or metal oxide to photostabilize the API or the pharmaceutical solid dosage form thereof.

[18] The method according to the [17] above, wherein the average diameter $D_{50}$ of the coated API particle is in the range of 1 μm to 1000 μm.

[19] The method according to the [17] or [18] above, wherein the metal oxide is iron oxide.

[20] The method according to any one of the [17] to [19] above, wherein the pharmaceutical solid dosage form is a tablet.

[21] The method according to any one of the [17] to [20] above, wherein the coating is performed by sputter deposition.

Effect of the Invention

According to the present invention, for example, it is possible to improve the photostability of an API itself or of pharmaceutical solid dosage forms produced with the API.

BRIEF DESCRIPTION OF THE DRAWING

FIG. 1 is photographs illustrating the appearance of API granules. From left to right, the photographs pertain to Comparative Example 1, Comparative Example 2, Example 1, Example 2, and Example 3.

FIG. 2 shows the results of photostability. The vertical axis represents the amount of increase in degradation product I (%) and the horizontal axis represents the amount of light exposure (10000 lux/hour). Crosses (x) indicate the results of Comparative Example 1, black triangles indicate the results of Comparative Example 2, black squares indicate the results of Example 1, black diamonds indicate the results of Example 2, and black circles indicate the results of Example 3, respectively.

FIG. 3 shows the results of photostability. The vertical axis shows the increase in degradation product I (%). For each test with its respective drug content, the left column shows the results without iron oxide, the middle column shows the results with the physical mixture, and the right column shows the results with sputter deposition.

EMBODIMENT FOR CARRYING OUT THE PRESENT INVENTION

1 API Particles for this Invention

The API particle of the present invention (hereinafter referred to as the "API of the present invention") are characterized by comprising a coating consisting of a metal or a metal oxide on the surface of the API particle.

The active pharmaceutical ingredient (API particle) according to the present invention is not particularly limited as long as it is an active pharmaceutical ingredient with pharmacological activity, but a light-unstable active pharmaceutical ingredient is preferred. Such an active ingredient can include, for example, calcium channel blockers such as nifedipine, amlodipine, nicardipine, and azelnidipine; vitamins; HMG-CoA reductase inhibitors such as atorvastatin, pitavastatin, and rosuvastatin. If they can take the form of salts, hydrates, solvates, etc., those forms are also included.

API particles prior to coating may be in the form of fine granules or granulated products. Such granulated products may be ones consisting of 100% active ingredients or ones consisting of active ingredients and other raw materials. The API of the present invention is also typically in the form of fine granules or granules (granulated product).

The average diameter $D_{50}$ of the API of the present invention is not particularly limited, but the range of 1 μm to 1000 μm is appropriate. Preferably, it is in the range of 2 μm to 600 μm, more preferably in the range of 5 μm to 500 μm.

The "average diameter $D_{50}$" refers to the volume average particle diameter, which means the particle diameter at 50% cumulative distribution from the smallest ($D_{50}$, median diameter) when measured by the laser diffraction method.

The metal or the metal oxide according to the present invention is not particularly limited as long as it is pharmaceutically acceptable and can be coated, e.g., sputtered. Metal oxides are suitable. Specifically, the metal can include, for example, gold, silver, and platinum, and the metal oxides can include, for example, iron oxides such as iron sesquioxide, yellow iron sesquioxide, yellow iron oxide, and black iron oxide; silicon dioxide; and titanium oxide. Of these, yellow iron sesquioxide, iron sesquioxide, and titanium oxide are preferred. The metal or the metal oxide can be called a coating agent.

The coating content of the metal or the metal oxide is not particularly limited, but can be in the range of 0.05% to 10% by mass on the surface of the API particles, for example. Preferably, the content is in the range of 0.08% to 6% by mass, and more preferably in the range of 0.1% to 4% by mass. If the content is less than 0.05% by mass, the desired effect (photostability, etc.) may not be sufficiently obtained. If the content is more than 10% by mass, the coating process may take a long time or the particles may be larger than necessary.

The API of the present invention can be used as a raw material for tablets, granules, dispersions, pellets, capsules, chewable tablets, lozenges, and film formulations, for example. Among these, it is preferred to be used as a raw material for tablets. As for tablets, they can be not only ordinary tablets but also multilayer tablets such as two-layer or three-layer tablets, enteric dissolving tablets, extended-release tablets, so-called OD tablets like orally disintegrating tablets, or OD films.

The present invention can include the above mentioned pharmaceutical solid dosage forms (especially tablets) containing the API of the present invention.

The coating of API particles to produce the API of the present invention is typically performed by sputter deposition.

Sputter deposition itself is a well-known technology and is one of the deposition technologies similar to vacuum deposition, which is classified as a dry plating method. It is a film deposition technique in which a high voltage is applied between the substrate to be deposited and the target of the film deposition material while inert gas (mainly argon gas) is introduced into the vacuum, causing the ionized inert gas to strike the target, and the target material that is flicked off is impacted and adhered to the substrate to form a film.

Sputtering methods include DC sputter deposition in which a DC voltage is applied between two electrodes, RF sputter deposition in which a radio frequency voltage is applied, magnetron sputter deposition, ion beam sputter deposition, mirror-tron sputter deposition, ECR sputter deposition, PEMS sputter deposition, and so on. In the present invention, these can be used according to the purpose, etc., taking into consideration the characteristics and disadvantages of each of them, without any particular restrictions. Among these, the magnetron sputtering method is preferred for coating API particles in the present invention.

In the magnetron type sputtering, for example, a strong magnetic field is applied in a vacuum with a light shielding agent, argon is introduced into the vacuum, argon atoms are ionized (Ar+) by the magnetic field, and such ionized argon is made to collide with the light shielding agent. The atoms and molecules on the surface of the shielding agent are then ejected and reach the surface of API particles to be coated, resulting in film formation.

Equipment for sputter deposition is commercially available, and such sputter deposition can be performed using such equipment.

2 Process for Producing Coated API Particles

The process for producing a coated API particle according to the present invention (hereinafter referred to as the "process of the present invention for API") is characterized by comprising a step of coating the surface of an API particle with a metal or a metal oxide, thereby producing the coated API particle.

Such coating is typically performed by sputter deposition as described above.

API (API particles), metal, metal oxide, and average diameter $D_{50}$ of coated API particles (API of the present invention), etc. are of the same meanings as described above.

The process of the present invention for API can include, for example, a step for granulating an API, a grading step, and a drying step in addition to the coating step. The step of granulating an API can be carried out by conventional methods. For example, water is added to an API and extrusion granulation can be used. The granulation step allows the API particles to be formed into granules and the particle size can be adjusted.

3 Others

3.1 Process for Manufacturing a Pharmaceutical Solid Dosage Form

The process for manufacturing a pharmaceutical solid dosage form according to the present invention (hereinafter referred to as the "process of the present invention for formulation") is characterized by comprising a step of coating the surface of an API particle with a metal or a metal oxide, and a step of formulating the dosage form using the coated API particle obtained in the preceding step.

The process of coating the surface of API particles with a metal or a metal oxide is of the same meaning as described above, and said coating is typically performed by sputter deposition. Also, API (API particles), metal, metal oxide, average diameter $D_{50}$ of coated API particles (API of the present invention), coating content of metal or metal oxide, and pharmaceutical solid dosage form, and so on are of the same meanings as described above.

The process of formulation using the coated API particle obtained in the previous step can be carried out depending on the intended formulation (e.g., tablets, granules, dispersions, pellets, capsules, chewable tablets, lozenges, film formulations) using methods known per se. For example, in the case of tablet formulation, a powder mixture is prepared by mixing coated API particles, excipients, disintegrants, etc., which is granulated or slagged (e.g., wet granulation) by addition thereto of a dispersing solution containing a coloring agent, etc., and then dried and graded, followed by the addition of excipients, disintegrants, lubricants, etc. and tableting (compression) to formulate a tablet. Granulation can also be carried out by dry granulation.

In the process of the present invention for formulation, raw materials or additives that can be used in addition to the coated API particle (the API of the present invention) vary depending on the intended formulation, etc. and can include, for example, the following excipients, binders, stabilizers, disintegrants, lubricants, coloring agents, etc.

Excipients that can be used in the present invention can include, for example, lactose, starch (e.g., corn starch, potato starch, rice starch, wheat starch), crystalline cellulose, D-mannitol, dextrin, sorbitol, anhydrous calcium phosphate, white sugar, talc (hydrous magnesium silicate), kaolin, precipitated calcium carbonate, sodium chloride, titanium dioxide, and light anhydrous silicic acid.

Binders that can be used in the present invention can include, for example, hydroxypropyl cellulose, hypromellose (hydroxypropyl methylcellulose, HPMC), microcrystalline cellulose, dextrin, tragacanth, gelatin, alpha starch, gum arabic, acacia, alginic acid, carboxymethyl cellulose, ethyl cellulose, methyl cellulose, hydroxyethyl cellulose, ethyl hydroxyethyl cellulose, polyvinylpyrrolidone, polyvinyl alcohol, polyacrylate, calcium carboxymethylcellulose, and sodium carboxymethylcellulose.

Stabilizers that can be used in the present invention can include, for example, butyl hydroxytoluene (BHT), propyl gallate, butyl hydroxyanisole (BHA), lecithin, alpha-tocopherol, hydroquinone, octyl gallate, dodecyl gallate, isoamyl gallate, nordihydroguaiaretic acid, guaiac fat, alpha-naphthylamine, ascorbic acid palmitate, cysteine hydrochloride, sodium ascorbate stearate, thioglycerol, and thiosorbitol.

Disintegrants that can be used in the present invention can include, for example, croscarmellose sodium, crospovidone, alginic acid, calcium carboxymethylcellulose, sodium carboxymethylcellulose, microcrystalline cellulose, hydroxypropyl cellulose, low substituted hydroxypropyl cellulose, cross-linked polyvinylpyrrolidone, sodium alginate, sodium starch glycolate, partially hydrolyzed starch, and agar powder.

Lubricants that can be used in the present invention can include, for example, magnesium stearate, calcium stearate, talc, mineral oil, stearic acid, fumaric acid, polyethylene glycol, calcium, boric acid, paraffin, and cocoa butter.

Coloring agents that can be used in the present invention can include, for example, tar dyes, red ferric oxide, iron oxide red, yellow ferric oxide, titanium dioxide, inorganic dyes, red #3, red #20, yellow #6, blue #2, green #5, orange #5, red #8, and caramel, which can be used in pharmaceuticals and other products as specified by the Ministry of Health and Welfare ordinance.

Each of the above additives may be used alone or in combination of any two or more. Also, each can be used in appropriate quantities as needed.

3.2 Photostabilization Method

The method of photostabilizing an API or a pharmaceutical solid dosage form according to the present invention (hereinafter referred to as the "photostabilization method of the present invention") is characterized by comprising a step of coating an API particle with a metal or metal oxide to photostabilize the coated API particle or the pharmaceutical solid dosage form.

The coating operation is typically performed by sputter deposition.

API or API particle, metal, metal oxide, average diameter $D_{50}$ of coated API particle (API of the present invention), coating content of metal or metal oxide, and pharmaceutical solid dosage form, and so on are of the same meanings as described above.

The photostabilization method of the present invention can improve the photostability of API particles and pharmaceutical solid dosage forms.

EXAMPLE

Hereinafter, the present invention will be described with reference to Examples, Comparative Examples, Test Examples, and the like, but the present invention is not limited by these Examples and the like in any way.

[Examples 1 to 3] Production of API Granules of the Present Invention

Amlodipine besilate was granulated with water by an extrusion granulator, then pelletized with a malmerizer and dried in a fluid bed granulator. The resulting powder was graded with 500 μm and 250 μm mesh to obtain amlodipine besilate granules (average particle size $D_{50}$: 400 μm). The APIs of the present invention (Examples 1 to 3) were obtained by coating the prepared amlodipine besilate granules with a magnetron sputtering system (power: 400 W, vacuum: $9.0\times10^{-1}$ Pa approximately). Separately, API granules without iron sesquioxide (Comparative Example 1) and a physical mixture of API granules and iron sesquioxide (Comparative Example 2) were prepared. The formulation contents of each granule are shown in Table 1. The appearance of each granule is shown in FIG. 1.

TABLE 1

| Composition | Component | Comp. Ex. 1 No $Fe_2O_3$ | Comp. Ex.2 Physical mixture $Fe_2O_3$: 0.585% | Example 1 Sputtering (3 h) $Fe_2O_3$: 0.129% | Example 2 Sputtering (6 h) $Fe_2O_3$: 0.289% | Example 3 Sputtering (10 h) $Fe_2O_3$: 0.585% |
|---|---|---|---|---|---|---|
| API (mg) | Amlodipine besilate | 6.93 | 6.93 | 6.93 | 6.93 | 6.93 |
| Coating agent (mg) | $Fe_2O_3$ | — | 0.0408 | 0.009 | 0.0201 | 0.0408 |
| Total (mg) | | 6.93 | 6.9708 | 6.939 | 6.9501 | 6.9708 |

[Examples 4 to 7] Production of Tablet Using the API Granules of the Present Invention The API granules without iron sesquioxide, the physical mixture of API granules and iron sesquioxide, and the APIs of the present invention were prepared in the same manner as described above. Each tablet was produced by adding excipients to each API granule and tableting at 5 kN using a single-shot tableting machine. The formulation contents of each tablet are shown in Tables 2 and 3.

TABLE 2

Drug content: 3.7%

| Composition | Component | Comp. Ex. 3 No $Fe_2O_3$ | Comp. Ex. 4 Physical mixture $Fe_2O_3$: 0.585% | Example 4 Sputtering (10 h) $Fe_2O_3$: 0.585% |
|---|---|---|---|---|
| API (mg) | Amlodipine besylate | 6.93 | 6.93 | 6.93 |
| Coating agent (mg) | $Fe_2O_3$ | — | 0.0408 | 0.0408 |

TABLE 2-continued

| | | | | |
|---|---|---|---|---|
| Excipient (mg) | Lactose hydrate | 90 | 90 | 90 |
| | Crystalline cellulose | 37.39 | 37.39 | 37.39 |
| | Magnesium stearate | 0.68 | 0.68 | 0.68 |
| Total (mg) | | 135.00 | 135.04 | 135.04 |
| Diameter of tablet (mm) | | 7 | 7 | 7 |

Drug content: 10%

| Composition | Component | Comp. Ex. 5 No $Fe_2O_3$ | Comp. Ex. 6 Physical mixture $Fe_2O_3$: 0.585% | Example 5 Sputtering (10 h) $Fe_2O_3$: 0.585% |
|---|---|---|---|---|
| API (mg) | Amlodipine besylate | 18.71 | 18.71 | 18.71 |
| Coating agent (mg) | $Fe_2O_3$ | — | 0.1102 | 0.1102 |
| Excipient (mg) | Lactose hydrate | 81.72 | 81.72 | 81.72 |
| | Crystalline cellulose | 33.89 | 33.89 | 33.89 |
| | Magnesium stearate | 0.68 | 0.68 | 0.68 |
| Total (mg) | | 135.00 | 135.11 | 135.11 |
| Diameter of tablet (mm) | | 7 | 7 | 7 |

TABLE 3

Drug content: 30%

| Composition | Component | Comp. Ex. 7 No $Fe_2O_3$ | Comp. Ex. 8 Physical mixture $Fe_2O_3$: 0.585% | Example 6 Sputtering (10 h) $Fe_2O_3$: 0.585% |
|---|---|---|---|---|
| API (mg) | Amlodipine besylate | 56.13 | 56.13 | 56.13 |
| Coating agent (mg) | $Fe_2O_3$ | — | 0.3305 | 0.3305 |
| Excipient (mg) | Lactose hydrate | 55.43 | 55.43 | 55.43 |
| | Crystalline cellulose | 22.76 | 22.76 | 22.76 |
| | Magnesium stearate | 0.68 | 0.68 | 0.68 |
| Total (mg) | | 135.00 | 135.33 | 135.33 |
| Diameter of tablet (mm) | | 7 | 7 | 7 |

Drug content: 50%

| Composition | Component | Comp. Ex. 9 No $Fe_2O_3$ | Comp. Ex. 10 Physical mixture $Fe_2O_3$: 0.585% | Example 7 Sputtering (10 h) $Fe_2O_3$: 0.585% |
|---|---|---|---|---|
| API (mg) | Amlodipine besylate | 93.56 | 93.56 | 93.56 |
| Coating agent (mg) | $Fe_2O_3$ | — | 0.5508 | 0.5508 |
| Excipient (mg) | Lactose hydrate | 29.12 | 29.12 | 29.12 |
| | Crystalline cellulose | 11.64 | 11.64 | 11.64 |
| | Magnesium stearate | 0.68 | 0.68 | 0.68 |
| Total (mg) | | 135.00 | 135.55 | 135.55 |
| Diameter of tablet (mm) | | 7 | 7 | 7 |

[Test Example 1] Photostability of API Granules of the Present Invention

The API granules of Examples 1 to 3 and Comparative Examples 1 and 2 were placed in a photostability test apparatus. The photostability test was conducted by irradiating them with xenon lamps at $30\times10^4$ to $120\times10^4$ lx·hr under 25° C. and 70% RH conditions. The results are shown in Table 5 and FIG. 2 (n=3).

It should be noted that the amount of degradation product I having the following structural formula was determined by high-performance liquid chromatography (HPLC). The measurement conditions are as follows. The increased amount of degradation product I was defined as the amount of degradation product I after light irradiation minus the initial amount of degradation product I before the start of light irradiation.

[Chemical 1]

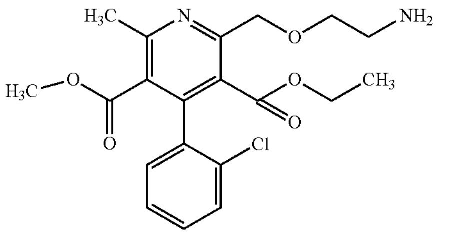

[HPLC Conditions]

Detector: Waters 2487, UV absorbance spectrophotometer (measurement wavelength: 237 nm)

Column: Cadenza CD C18, 4.6 mm i.d., 15 cm stainless steel tube packed with 3 µm octylsilylated silica gel for liquid chromatography.

Column temperature: Constant temperature around 35° C.
Sample temperature: Constant temperature around 4° C.
Mobile phase: Potassium dihydrogen phosphate solution/acetonitrile mixture

TABLE 4

| Time (min.) | Potassium dihydrogen phosphate (%) | Acetonitrile (%) |
|---|---|---|
| 0 to 15 | 80→50 | 20→50 |
| 15 to 20 | 50→20 | 50→80 |
| 20 to 25 | 20 | 80 |
| 25 to 26 | 20→80 | 80→20 |
| 26 to 30 | 80 | 20 |

Flow rate: 1.0 mL per minute
Analysis time: 30 minutes

TABLE 5

| | Degradation product I (%) | | | | |
|---|---|---|---|---|---|
| $\times 10^4$ lx · hr | Comp. Ex. 1 | Comp. Ex. 2 | Example 1 | Example 2 | Example 3 |
| 0 | 0.005 | 0.011 | 0.063 | 0.071 | 0.091 |
| 30 | 0.541 | 0.581 | 0.439 | 0.373 | 0.283 |
| 60 | 1.269 | 1.235 | 0.938 | 0.561 | 0.553 |
| 120 | 3.199 | 2.973 | 1.693 | 1.053 | 0.841 |
| | Increase amount of degradation product I (%) | | | | |
| $\times 10^4$ lx · hr | Comp. Ex. 1 | Comp. Ex. 2 | Example 1 | Example 2 | Example 3 |
| 30 | 0.536 | 0.570 | 0.376 | 0.302 | 0.192 |
| 60 | 1.264 | 1.224 | 0.875 | 0.490 | 0.462 |
| 120 | 3.194 | 2.962 | 1.630 | 0.982 | 0.750 |

As is clear from Table 5 and FIG. 2, the photostability of amlodipine was markedly improved for the API of the present invention in proportion to the length of sputtering time.

[Test Example 2] Photostability of Tablets Using the API of the Present Invention The tablets of Examples 4 to 7 and Comparative Examples 3 to 10 were evaluated for photostability as in Test Example 1 (It should be noted that the amount of light exposure was only $120\times10^4$ lx·hr).

As a result, as shown in FIG. 3, the photostability of the tablets produced with the API of the present invention was as good as or better than that of the physical mixture.

[Example 8] Production of the API of the Present Invention

Using a magnetron sputtering apparatus, amlodipine besilate powder with a particle size of approximately 5 μm was coated with 3.64 mass % red ferric oxide to obtain the amlodipine besilate powder of the present invention (Example 8). A physical mixture of said amlodipine besilate powder and red ferric oxide was separately prepared (Comparative Example 11).

The photostability test was conducted on the API of the present invention (Example 8) and the physical mixture (Comparative Example 11) under 25° C. and 70% RH conditions and irradiation with a xenon lamp at $60\times10^4$ lx·hr. As a result, the increase in degradation product I was 2.09% for the API of the present invention (Example 8) and 2.68% for the physical mixture (Comparative Example 11). Thus, the amount of increase in degradation products was more suppressed in the API of the present invention.

INDUSTRIAL APPLICABILITY

The present invention is useful in pharmaceutical solid dosage forms or manufacture thereof, because it can provide an API with excellent photostability, for example, as raw materials for pharmaceutical products.

The invention claimed is:

1. A coated active pharmaceutical ingredient (API) particle, comprising:
an API particle, and
a coating film consisting of a metal oxide on the surface of the API particle,
wherein 0.1% to 4% by mass of the coated API particle is the coating film and the coated API has an average diameter $D_{50}$ in the range of 1 μm to 1000 μm.

2. A process for producing a coated API particle, comprising coating an API particle with a metal oxide, wherein 0.1% to 4% by mass of the coated API particle is the coating film and the coated API has an average diameter $D_{50}$ in the range of 1 μm to 1000 μm.

3. A process for manufacturing a pharmaceutical solid dosage form, comprising:
coating the surface of an API particle with a metal oxide to obtain a coated API particle; and
formulating the dosage form using the coated API particle obtained in the preceding step to manufacture the pharmaceutical solid dosage form;
wherein 0.1% to 4% by mass of the coated API particle is the coating film and the coated API has an average diameter $D_{50}$ in the range of 1 μm to 1000 μm.

4. The process according to claim 3, wherein the pharmaceutical solid dosage form is a tablet.

5. A pharmaceutical solid dosage form, comprising the coated API particle according to claim 1.

6. The pharmaceutical solid dosage form according to claim 5, wherein the pharmaceutical solid dosage form is a tablet.

7. A method of photostabilizing an API or a pharmaceutical solid dosage form thereof, comprising forming a coating film on an API particle with a metal oxide to generate a coated API particle, wherein 0.1% to 4% by mass of the coated API particle is the coating film, wherein the average diameter $D_{50}$ of the coated API particle is in the range of 1 μm to 1000 μm and wherein the coating film consists of the metal oxide.

8. The method according to claim 7, wherein the pharmaceutical solid dosage form is a tablet.

9. The coated API article according to claim 1, wherein the particle consists of the API particle and the coating film.

* * * * *